United States Patent [19]

Zoha et al.

[11] Patent Number: 5,192,510
[45] Date of Patent: Mar. 9, 1993

[54] APPARATUS FOR PERFORMING FLUORESCENT ASSAYS WHICH SEPARATES BULK AND EVANESCENT FLUORESCENCE

[75] Inventors: Steven J. Zoha, Jarrettsville, Md.; James E. Davis; Alan R. Craig, both of Wilmington, Del.; Alan M. Hochberg, Hockessin, Del.

[73] Assignee: E. I. Du Pont de Nemours and Company, Wilmington, Del.

[21] Appl. No.: 648,005

[22] Filed: Jan. 30, 1991

[51] Int. Cl.$^5$ .................... G01N 21/01; G01N 21/64
[52] U.S. Cl. .................... 422/82.05; 356/244; 356/246; 422/82.08; 422/82.11
[58] Field of Search .................... 422/82.05-82.09, 422/82.11; 356/244, 246, 440; 250/277.31

[56] References Cited

U.S. PATENT DOCUMENTS

| 3,415,602 | 12/1968 | Harrick . | |
|---|---|---|---|
| 3,486,829 | 12/1969 | Wilks | 356/246 |
| 3,604,927 | 9/1971 | Hirschfield | 250/71 |
| 3,770,382 | 11/1973 | Carter et al. | 422/65 |
| 3,849,654 | 11/1974 | Malvin | 250/363 |
| 3,898,457 | 8/1975 | Packard et al. | 422/82.05 X |
| 3,939,350 | 2/1976 | Kronick et al. | 250/365 |
| 4,050,895 | 9/1977 | Hardy et al. | 23/230 |
| 4,066,362 | 1/1978 | Carter | 422/82.09 X |
| 4,100,416 | 7/1978 | Hirschfield | 250/461 |
| 4,321,057 | 3/1982 | Buckles | 23/230 |
| 4,363,551 | 12/1982 | Achter et al. | 356/338 |
| 4,368,047 | 1/1983 | Andrade et al. | 435/4 |
| 4,399,099 | 8/1983 | Buckles | 422/58 |
| 4,447,546 | 5/1984 | Hirschfield | 436/527 |
| 4,451,434 | 5/1984 | Hart | 422/102 |
| 4,558,014 | 12/1985 | Hirschfield et al. | 436/527 |
| 4,582,809 | 4/1986 | Block et al. | 436/527 |
| 4,602,869 | 7/1986 | Harrick | 346/244 |
| 4,608,344 | 8/1986 | Carter et al. | 436/34 |
| 4,654,532 | 3/1987 | Hirschfield | 250/458.1 |
| 4,671,938 | 6/1987 | Cook | 422/57 |
| 4,685,880 | 8/1987 | Meguro et al. | 422/66 X |
| 4,703,182 | 10/1987 | Kroneis et al. | 250/458.1 |
| 4,716,121 | 12/1987 | Block et al. | 436/514 |
| 4,775,637 | 10/1988 | Sutherland et al. | 422/82.11 X |
| 4,810,658 | 3/1989 | Shanks et al. | 436/172 |
| 4,818,710 | 4/1989 | Sutherland et al. | 436/527 |
| 4,837,168 | 6/1989 | de Jaeger et al. | 436/534 X |
| 4,844,869 | 7/1989 | Glass | 422/68 |
| 4,857,273 | 8/1989 | Stewart | 422/68 |
| 4,877,747 | 10/1989 | Stewart . | |
| 4,909,990 | 3/1990 | Block et al. | 422/82.11 |
| 4,945,245 | 7/1990 | Levin | 250/461.2 |

FOREIGN PATENT DOCUMENTS

| 0254430 | 1/1988 | European Pat. Off. . |
| 0326375 | 8/1989 | European Pat. Off. . |
| 6266141 | 9/1985 | Japan . |
| WO88/09925 | 12/1988 | PCT Int'l Appl. . |
| 9001157 | 2/1990 | World Int. Prop. O. . |

OTHER PUBLICATIONS

1 Hecht, et al., "Optics", 1974, pp. 81–84, Addison-Wesley Publishing Company, Reading, Mass.
Sutherland, et al., *Nonisotopic Immunoassay*, 1988, pp. 331–357.
Love, et al., *Chem., Biochem. and Environ. Appli. of Fibers*, 1989, pp. 175–180.
Andrade, et al., *IEEE*, 1985, pp. 1175–1179.
Sutherland, et al., *J. Immunol. Methods*, 1984, pp. 253–265.
Sutherland, et al., *Clin Chem*, vol. 30 (9), 1984, pp. 1533–1538.

*Primary Examiner*—Jill A. Johnston
*Assistant Examiner*—Arlen Soderquist

[57] ABSTRACT

This invention uses the evanescent wave detection of particles to distinguish bound from free in an analyte-binding assay. Illumination below the critical angle is employed, and a beveled window is used to eliminate bulk fluorescence from the emitted evanescent wave liquid. The sample is held in a non-rigid film cuvette.

1 Claim, 3 Drawing Sheets

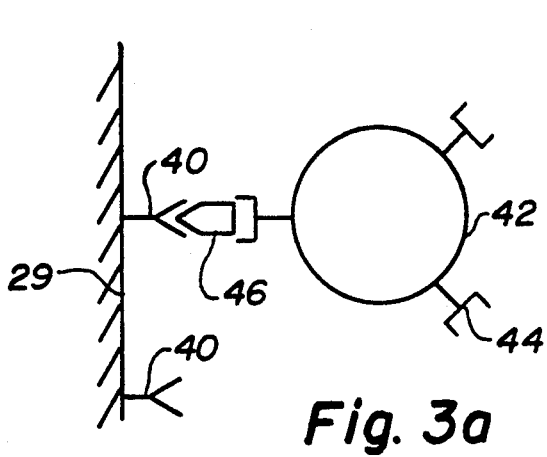 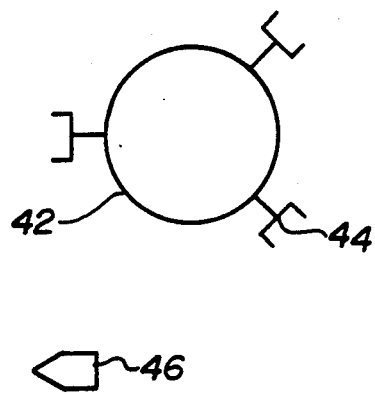
Fig. 3a SANDWICH
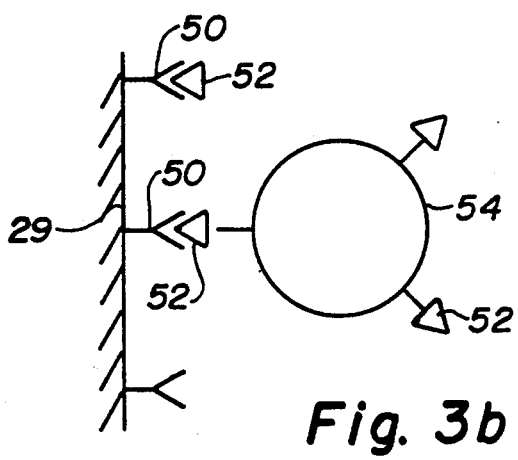 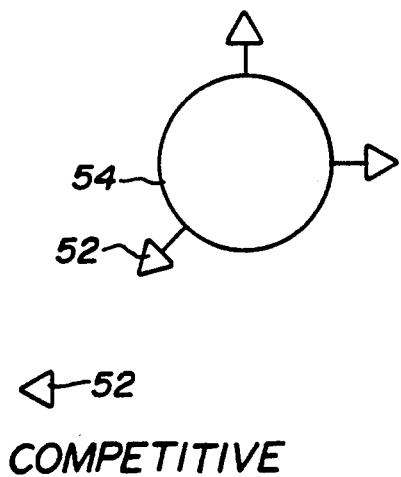
Fig. 3b COMPETITIVE
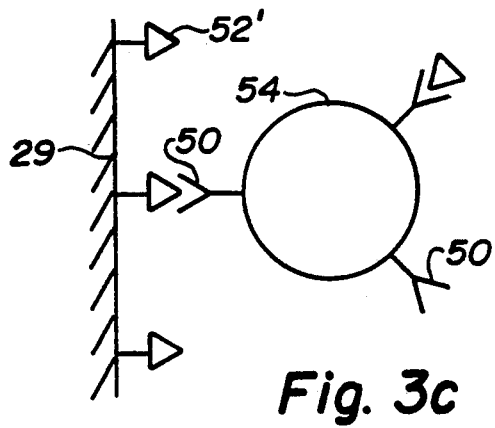 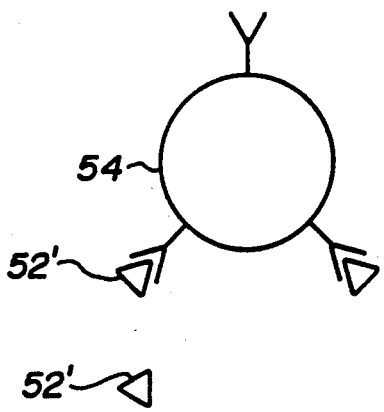
Fig. 3c COMPETITIVE-IMMUNOMETRIC

APPARATUS FOR PERFORMING FLUORESCENT ASSAYS WHICH SEPARATES BULK AND EVANESCENT FLUORESCENCE

FIELD OF THE INVENTION

This invention relates to the use of evanescent wave detection of fluorescent particles to distinguish bound from free material in an analyte-binding assay.

BACKGROUND OF THE INVENTION

In order to determine the concentration of analytes in biological fluids, specific binding partners for analytes are often used. The analyte concentration is determined by generating a signal which is modulated in accordance with the amount of analyte bound to the binding partner. Many forms of binding assays have been described, most of which depend on a physical technique such as centrifugation or filtration to separate bound from free material. These techniques can be complex and expensive to automate. On the other hand, the optical phenomenon known as "total internal reflection" has been used to distinguish bound from free material in several immunoassay systems that do not require a mechanical separation step. Immunoassay systems employ antibodies as the analyte binding partners; the principles used, however, can be applied to other forms of binding assays such as those using hormone receptors or DNA probes.

Total internal reflection is a phenomenon that occurs when light is aimed at a glancing angle, above the so-called "critical angle", from a medium of high refractive index, such as glass, toward a medium of lower refractive index, such as water. The beam of light is reflected at the interface between the two media. Total internal reflection is described in E. Hecht and A. Zajac, *Optics*, Addison-Wesley Publishing Co., Reading, Mass. (1974), pp. 81–84.

Under conditions of total internal reflection, it can be demonstrated that a portion of the light called the "evanescent wave" penetrates the low-refractive-index medium to a depth of a fraction of a wavelength, typically 100 nm or so. This light will therefore illuminate materials which are bound at the interface between the two media; materials not at the interface will not be illuminated. This provides a separation, a means of distinguishing bound from free material, without the need for a mechanical separation device.

U.S Pat. No. 3,939,350 (Kronick et al.) describes an immunoassay system employing haptens or antibodies attached to a glass prism having a surface in contact with an aqueous medium. Immunologically-bound fluorescent antibodies are detected by their presence within the region illuminated by the evanescent wave. To achieve this, Kronick designed a system such that light enters the sample chamber above the critical angle. This requires sophisticated light sources such as lasers or arc lamps to produce a small diameter, collimated beam for illumination of a small sample. The samples are placed on a slide but nevertheless the sample chamber must be cleaned after each assay.

U.S. Pat. No. 4,451,434 (Hart) utilizes fluorescent latex particles as a label, giving potentially much greater signal per binding event than that obtainable by Kronick et al. Although an improvement over Kronick et al., Hart still is faced with the problem of using sophisticated light sources with the inherent disadvantages just related. Also, high quality sample cuvettes must be used which are formed to incorporate prisms. Even when well manufactured, plastic devices will not in general have the high optical quality of the glass, quartz or sapphire prisms.

EP 0 326 375 and EP 0 254 430 (Schutt et al.) describe a similar immunoassay system in which light-scattering particles, such as polymer latex or colloidal gold, are used in place of the fluorophores described by Kronick et al. The examples in these patents indicate that assays employing evanescent wave phenomena can achieve sensitivity otherwise obtainable only in assays that employ a mechanical separation step. Otherwise, Schutt et al. suffer from the same disadvantages as Hart and Kronick et al.

U.S Pat. No. 4,447,546 (Hirschfeld) is an example of the use of an optical fiber or rod-like waveguide in an immunoassay. Since light is confined inside an optical fiber by a series of internal reflections, an evanescent wave field exists along the entire surface of the fiber. Antibodies or antigens are attached to the fiber, and the fiber is then immersed in the sample to be tested. Fluorescence or other optical changes can be detected at an end of the fiber. Because some such devices can be immersed directly into a neat biological fluid, they are sometimes referred to as "biosensors". Whatever Hirschfeld's advantages, his system still requires cleaning or replacement of the biosensor after each use.

U.S Pat. No. 4,810,658 (Shanks et al.) describe a waveguide which is placed in contact with an illuminated sample. Fluorescence from bound material produces an evanescent wave in the waveguide which exits the waveguide above the critical angle. Fluorescence from unbound material is refracted at the interface, and can therefore only exit the waveguide at an angle below the critical angle.

Systems such as those described by Schutt et al. and Shanks et al. rely upon optical apertures to limit the acceptance angle of the detector so that non-evanescent waves are excluded. The edge of the waveguide in these cases is an extended light source, as opposed to a point source. That is, light is emitted from regions that do not lie on the optical axis of the system. Under these conditions, no aperture can be designed that accepts all rays up to a given incidence angle, a, and rejects all others. Thus separation of evanescent and non-evanescent radiation will be less than ideal. Under most assay conditions, the evanescent signal is much weaker than the non-evanescent background, so good separation is essential. Furthermore, apertures must be properly aligned with respect to the waveguide and the detector in order to function well.

Another disadvantage of Shanks et al. is that the illuminating beam passes through the sample in order to reach the waveguide. This increases the interfering effects in the bulk solution of light scattering or absorbing substances on the evanescent wave signal.

SUMMARY OF THE INVENTION

Many of these disadvantages of the prior art are overcome by the apparatus of this invention. According to this invention, an apparatus is provided for detecting an analyte of interest in a sample by using a source of excitation radiation and a tag capable of causing inelastic scattering of the excitation radiation, the apparatus comprising: an optically transparent sample holder having an interior volume and an inner wall, an optically transparent member adapted to contact the sample holder to provide an optical interface with the sample, the transparent member having a refractive index greater than the refractive index of the sample, means for directing radiation from the source to the transparent member at angles below the critical angle relative to the optical interface, thereby to illuminate the interior of the sample holder, first and second binding members, the tag being attached to the first binding member, the second binding member being immobilized on the inner wall of the sample holder at the optical interface, such that the presence of analyte in the sample modulates the attachment of the tag to the wall, and a first detector for detecting radiation produced by such inelastic scattering, the transparent member being shaped to direct evanescent wave radiation, from the inner wall of the sample holder, lying between the plane of the analyte binding inner wall and the total internal reflection critical angle of the optical interface, to the detector.

Using this apparatus, low F-number illumination optics can be employed. The low F-number permits the use of inexpensive lamps such as quartz-halogen lamps. Furthermore, the illuminating beam need not pass through the sample prior to reaching the transparent member. Thus the illuminating beam may strike the bioactive surface before passing through the sample. This reduces the interfering effects of light scattering or absorbing substances on the evanescent wave signal.

The window geometry employed in this invention uses the internal reflection principle to efficiently collect rays below a given angle of incidence a, and to reject all rays of greater incidence angle, even for an extended light source. No precise alignment is necessary to achieve this separation, since the angle a is determined solely by the shape and refractive index of the window.

The apparatus also takes advantage of a unique form of sample container not previously utilized for evanescent wave immunoassays. The sample is contained in a bag formed from transparent, flexible film. Such a bag, or sample pack, can be pressurized between two parallel windows to form a cuvette for spectrophotometric analysis. In the present invention, the second window may be non-transparent. A refractive-index-matching oil may be used to improve the optical coupling between the window and the sample pack. The window incorporates a prism that transmits incident illumination in one direction, and transmits the evanescent wave fluorescence in another direction. The advantage here is in using a window which is separate from the biochemically-reactive sample pack wall.

The pack wall can be made of a cast or blown film, which can easily achieve the required optical transparency and flatness at low cost. Freedom from optical defects is essential to achieving high-sensitivity evanescent-wave assays, since optical defects couple signal from the bulk solution into the detector, and hence contribute background noise. This invention eliminates the challenge of mass-producing high-optical-quality sample cuvettes which incorporate prisms, waveguides or optical fibers, as in the prior art devices, respectively. Even well-molded, plastic devices will not in general have the high optical quality of the glass or quartz prisms that can be incorporated in this invention.

Use of a pack film separate from the prism also simplifies the problem of coating bioactive material onto the surface, since, in general, coating film is easier to mechanize than coating discrete devices. Also, the chemistry of the film for coating can be controlled without regard to its molding or extrusion properties that would affect the formation of a prism, waveguide, or fiber. Likewise, since the prism is not in contact with the sample, it can be designed without considerations of biocompatibility or coating.

In short, illumination below the critical angle is employed. A shaped window is used to eliminate bulk fluorescence from the emitted evanescent wave signal. Finally, the sample is held within a non-rigid film cuvette.

BRIEF DESCRIPTION OF THE DRAWINGS

The invention may be more easily understood with reference to the accompanying drawings in which like reference numerals denote like items, in which:

FIGS. 3A, 3B and 3C depict respectively a sandwich assay, a competitive assay and a competitive-immunometric operated using the apparatus of this invention.

DESCRIPTION OF THE INVENTION

Figure 1:
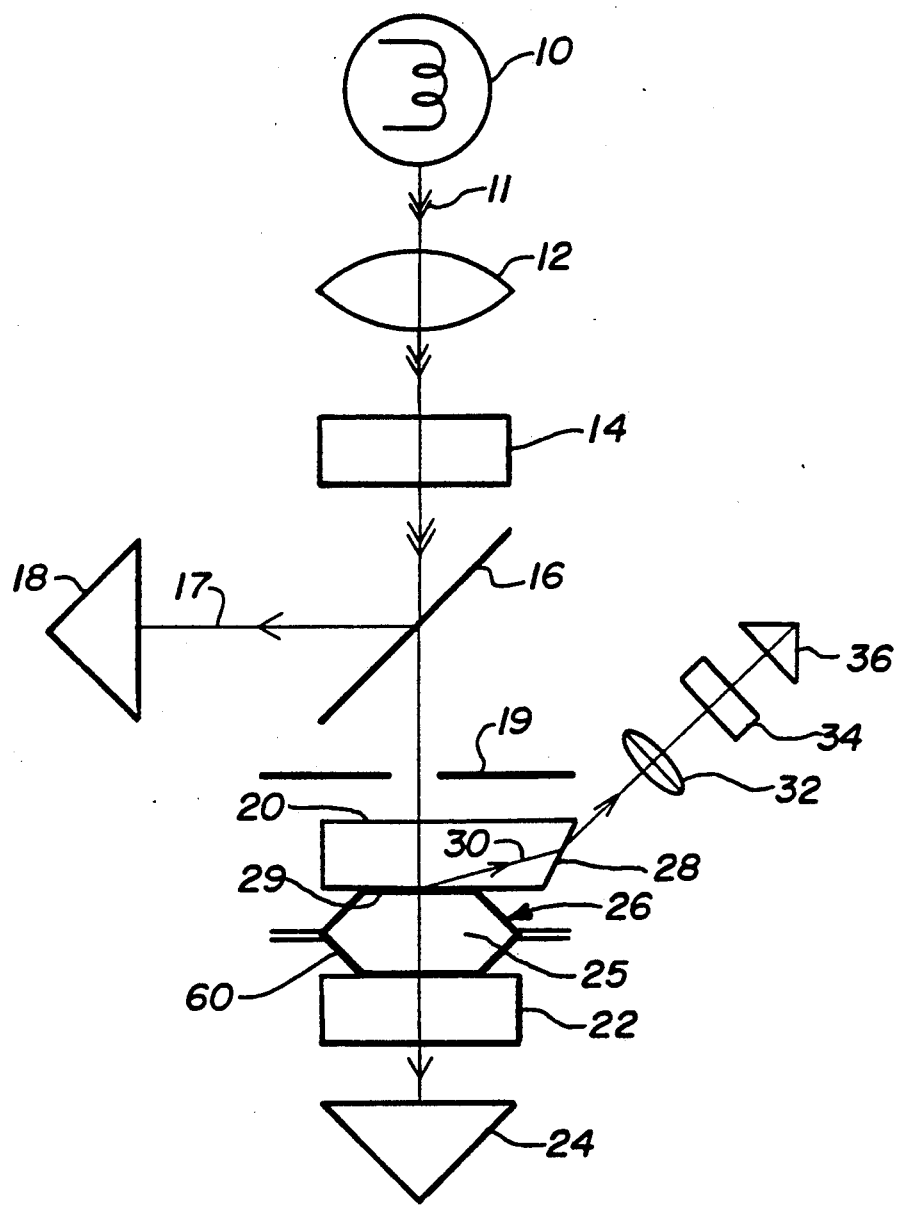
FIG. 1 is a schematic diagram of an apparatus for detecting an analyte of interest using the evanescent detection system of this invention.

FIG. 1 shows a schematic representation of the present invention in which there is shown a light source 10. The invention may employ any light source capable of exciting fluorescence or phosphorescence. These sources 10 include tungsten or quartz-halogen lamps, arc lamps, flashlamps, light-emitting diodes, lasers, etc. The light source 10 will generally be stable and continuous, but may be pulsed or chopped to permit synchronous detection as a means of noise reduction. Light 11 from the source 10 is directed toward a sample cuvette 26 which is more clearly shown in FIG. 2. In the case shown, a quartz-halogen lamp 10 is used, since this type of lamp generates adequate light power in a simple and inexpensive configuration. Since the rays from such a lamp are divergent, a lens 12 is used to collect rays and direct them toward the sample cuvette 26. The light may be filtered by a color filter 14 to remove any incident radiation at the emission wavelength which would interfere with detection, excess infrared radiation that could overheat the sample, and any non-exciting wavelengths that could cause nonspecific fluorescence of the sample, window, cuvette, or other components.

A beamsplitter 16 or other device may be used to sample the incident beam as by the split light 17 in order to establish a reference signal for ratio measurement or synchronous detection by reference diode detector 18. The incident light then passes through an aperture 19.

Incident light leaving the aperture 19 passes through a first member or window 20 to a sample cuvette 26. This window 20 must be transparent at the excitation and emission wavelengths of the fluorophore or phosphor, must be substantially non-fluorescent and non-phosphorescent, and must be of good optical quality, since scattering centers may couple extraneous light into the evanescent wave signal. The window must be of higher refractive index than the bulk sample 25 contained in the cuvette 26 in order for evanescent wave generation to take place. Generally, optical glass, quartz or sapphire will be used for the window 20.

The aperture 19 is used so that portions of the sample cuvette 26 not in contact with the windows 20, 22 will not be illuminated. Areas of poor contact between the cuvette and the windows can produce small, flexible prisms which couple unpredictable amounts of bulk fluorescence into the evanescent wave. This can lead to spurious signals.

After the light leaves the window 20, it enters the sample 25 through the cuvette wall 29, which is in contact with the window 20 and preferably is made of a flexible film 60. A liquid such as microscope immersion oil may be used to ensure good optical coupling, i.e., optical interface, between the film 60 and the window 20, since the evanescent wave will not cross any air gaps.

The cuvette film 60 must be transparent, substantially non-fluorescent, and of good optical quality. The blowing or casting processes used to form films can be designed so that the surface tension of the film 38 generates a flat, high-quality optical surface. Such processes are well known and described, for example, by Baird, R. J. and Baird, D. T., Industrial Plastics, The Goodheart-Willcox Co., Inc., South Holland, Ill. (1982), p. 106, 177-183. The film 60 must be of higher refractive index than the bulk sample 25 so that an evanescent wave will be formed. The film 60 must be mechanically strong and flexible if high pressures are used to force good contact between the film 60 and the window 20. Surfactant treatment of the film 60 may be necessary to eliminate air bubbles in the sample, and to reduce non-specific binding of fluorescent material. The film 60 must be capable of binding a bioactive molecule, without substantial shedding or loss of activity of that molecule. A blown, ionomeric film such as Surlyn (R) can be used successfully. Other films such as polyvinyl chloride or polystyrene may also be used. Bioactive materials can be coupled to such polymers by absorption or by covalent bonding to moieties such as carboxyl, hydroxyl or amino groups present on or added to the polymer surface. Bioactive materials may be applied to the film 60 by a number of coating processes, including spraying, soaking, or printing.

Light 11 passes through the first window 20 normal (perpendicular) to the window. This maximizes the light reaching the sample cuvette 26. Beyond the sample cuvette 26 is a second window 22 made of the same material as the first window 20. Light passing directly through the sample 25 in the sample cuvette 26 and the second window 22 is directed to a sample diode detector 36. This permits sample absorbance to be measured simultaneously or alternatively with the evanescent wave measurement which will be described below. Thus, more than one analyte may be detected at one time or assay quality measurements may be made.

Inside the cuvette, an assay or biochemical process is used to bind the fluorescent tag particles to the inner film wall 29. Examples of such processes are shown schematically in FIG. 3. The extent of binding of the particles is modulated by the presence of an analyte of interest. FIG. 3a shows a "sandwich"-type assay, which is a well-known form of assay typically for antigens or nucleic acids. Attached to the film inner wall 29 is a substance 40 capable of binding to the analyte of interest 46; attached to a fluorescent latex particle 42 is a second binding partner 44 capable of simultaneously binding to the analyte 46. The use of the latex particles is preferred. In this case, a "sandwich" is formed in the presence of the analyte 46, and the extent of fluorescent particle binding increases with increasing analyte concentration.

FIG. 3b shows a "competitive binding" assay, typically used for immunochemical detection and also for assays involving hormones and receptors, lectins, sugars, etc. In this type of assay, the surface of the film inner wall 29 bears a binding partner 50 for the analyte 52. Fluorescent latex particles 54 bear the analyte 52 or an analog thereof. In the absence of analyte 52 in the sample, the particles 54 bind extensively to the surface 29. The presence of analyte 52 inhibit the binding of particles 54 by occupying receptors of the binding partners 50 on the film inner surface 29. Thus high analyte concentrations result in a lower extent and rate of binding.

FIG. 3c shows a competitive-binding assay with the roles of the fluorescent particles 54 and the film inner wall 29 reversed, that is, the film inner wall 29 bears the analog 52' of an analyte and the particles 54 bear the analyte receptor or binding partner 50.

In this invention, a fluorescent latex is used to generate signal. The fluorescent latex particles 42, 54 give a much greater signal per binding event than does a single fluorescent molecule per binding molecule. The fluorescent latex may consist of particles from about 0.01 to 1.0 u in diameter. Larger particles may settle during the assay, depending on their density. Latex particles are well known and described by Bangs, L. B., Uniform Latex Particles, Seradyne, Inc., Indianapolis, Ind. (1987) pp. 3-8. They can be easily made by emulsion polymerization processes, from materials such as polystyrene or polymethyl methacrylate. Care must be taken to ensure that the particles do not irreversibly aggregate during their manufacture, dyeing, labelling, storage, or use. Proper buffer ionic strength and surfactant concentration can prevent aggregation.

Particles can be dyed with fluorophores by a variety of methods. One such method is described, for example, by Bangs, L. B., Op. Cit., pp. 40-42. The efficiency of evanescent wave detection of fluorescence will vary with the particle refractive index in a manner described by in E. H. Lee, et al., "Angular distribution of fluorescence from liquids and monodispersed spheres by evanescent wave excitation", *Applied Optics* 18 (6), Mar. 15, 1979, pp. 862-868. Therefore the refractive index of the particles should be chosen to maximize the amount of fluorescent emission which is directed toward the detector. The size of the particle will affect assay sensitivity in a complex way, because size will affect the diffusion coefficient of the particle and the surface-to-volume ratio of the system. Therefore size affects the reaction rate, as well as the amount of fluorescence per particle. Since the particle diameter may be on the same order of magnitude as the wavelength of incident illumination, one may take advantage of resonance effects which result in enhanced brightness for certain particle sizes.

The fluorescent dye in the latex should be chosen to have a high extinction coefficient for the exciting wavelength, high quantum yield, and a sufficient Stokes shift to simplify the excitation and emission color filters for minimization of scattered light from passing through pair. It may be preferable to use an emission wavelength longer than about 550 nm, to reduce fluorescence from biological samples and plastic materials in the instrument and cuvette. The dye may have a fluorescence lifetime greater than that of biological materials and plastics, so that time-resolved detection can distinguish the dye from background sources of fluorescence. The dye may be phosphorescent rather than fluorescent, with a lifetime on the order of seconds or more. Since the dyes may be embedded in the polymeric latex, it is not required that the dye be water-soluble or fluorescent in an aqueous phase.

Alternatively, a chemiluminescent molecule may be used in place of the dye. In this case, an external light source need not be used, but rather, the chemicals required to activate luminescence must be added to the sample.

As noted by Hart, an absorbing dye may be added to the sample in order to reduce interference from fluorescence in the bulk of the sample.

A fluorescent latex having a spectrum distinct from that of the particles used in the assay, but which binds to the binding moiety on the cuvette film, may be added to the sample, and measured at a second set of wavelengths, to correct for variations in system gain and in the density of binding sites on the film. Care must be taken to ensure that such a latex does not interfere with the binding of analyte to its partner.

A fluorescent dye or non-binding fluorescent latex having a spectrum distinct from that of the bioactive particles may be added to the sample, and measured at a second set of wavelengths, to correct for fluorescence background from the bulk.

Because light is directed into the sample, both bound and free latex particles will emit radiation, i.e., fluoresce, if a fluorescent material is used, and will emit their radiation at all possible angles. However as described by Hecht et al., fluorescence from the bulk of the sample cannot enter the window at an angle above the critical angle of the sample-window optical interface. Fluorescent material bound to the surface 29, on the other hand, generates an evanescent wave that can be emitted above the critical angle. The difficulty in efficiently separating and detecting only the evanescent wave emission from such wall surface 29 is obviated by this invention.

In accordance with this invention, the first transparent member or window 20 is formed to have a beveled edge 28 which is used to separate emission above the critical angle from that below. The bevel angle is chosen so that all light crossing the sample-window interface less than the critical angle will be internally reflected at the beveled edge or face 28, and will thus not enter a detector 36. The rays from the exiting evanescent wave are directed through a condenser lens 32 and color filter 34 to a suitable detector 36. Nearly all rays entering the window above the critical angle will pass through the beveled face 28, and will reach the detector 36. These rays will be bent (refracted), and this must be kept in mind in determining the proper position for the detector.

Because the beveled window edge 28 excludes bulk fluorescence of the sample in the interior of the sample cuvette from the detector, in the absence of particle binding to the cuvette wall 29 there would ideally be no evanescent wave, and therefore no background fluorescence signal. In practice, there are two main sources of background. First, any microscopic defects in the cuvette film or window may act as prisms which couple the bulk fluorescence into the detector. Second, a certain number of particles will be close enough to the film to generate an evanescent wave, even though they are unbound, merely as a consequence of the uniform spatial distribution of particles within the cuvette. There may also be binding of particles to the film which is not mediated by the presence of analyte. Such so-called "nonspecific binding" is a nearly universal phenomenon in binding assays. The assay buffer is formulated to maximize the assay signal while minimizing nonspecific binding. Buffer salts, proteins, and surfactants are generally used for this purpose.

The evanescent emission, whether collected with the lens 32 or an optical fiber (not shown), may be passed through an aperture (not shown) to remove stray light. The light must be filtered as by filter 34 to remove any light at the excitation wavelength, so that scattered light is not detected. This will remove the typically large scatter background signal. Suitable filters may include interference filters and colored glass filters. Light then reaches the detector 36 sensitive to the fluorescent emission wavelength. Examples of detectors 36 include photomultipliers with either current (analog) or photon-counting electronics, vacuum photodiodes, silicon or other photodiodes, or photoconductive materials. Low light levels usually require high sensitivity normally provided by the PMT.

Electronic signals from the evanescent wave detector 36, and from the reference detector 18 and absorbance detector 24, if any, are typically sent to a digital computer for processing. One advantageous form of processing is to measure the ratio of the evanescent signal to that of the reference detector 18, to cancel out signal variations due to changes in lamp intensity. Another advantageous form of signal processing is to measure the rate of change of the evanescent fluorescence signal over time, as the biochemical reaction takes place. This effectively removes any background signal, since the background signal does not generally change with time.

Figure 2:
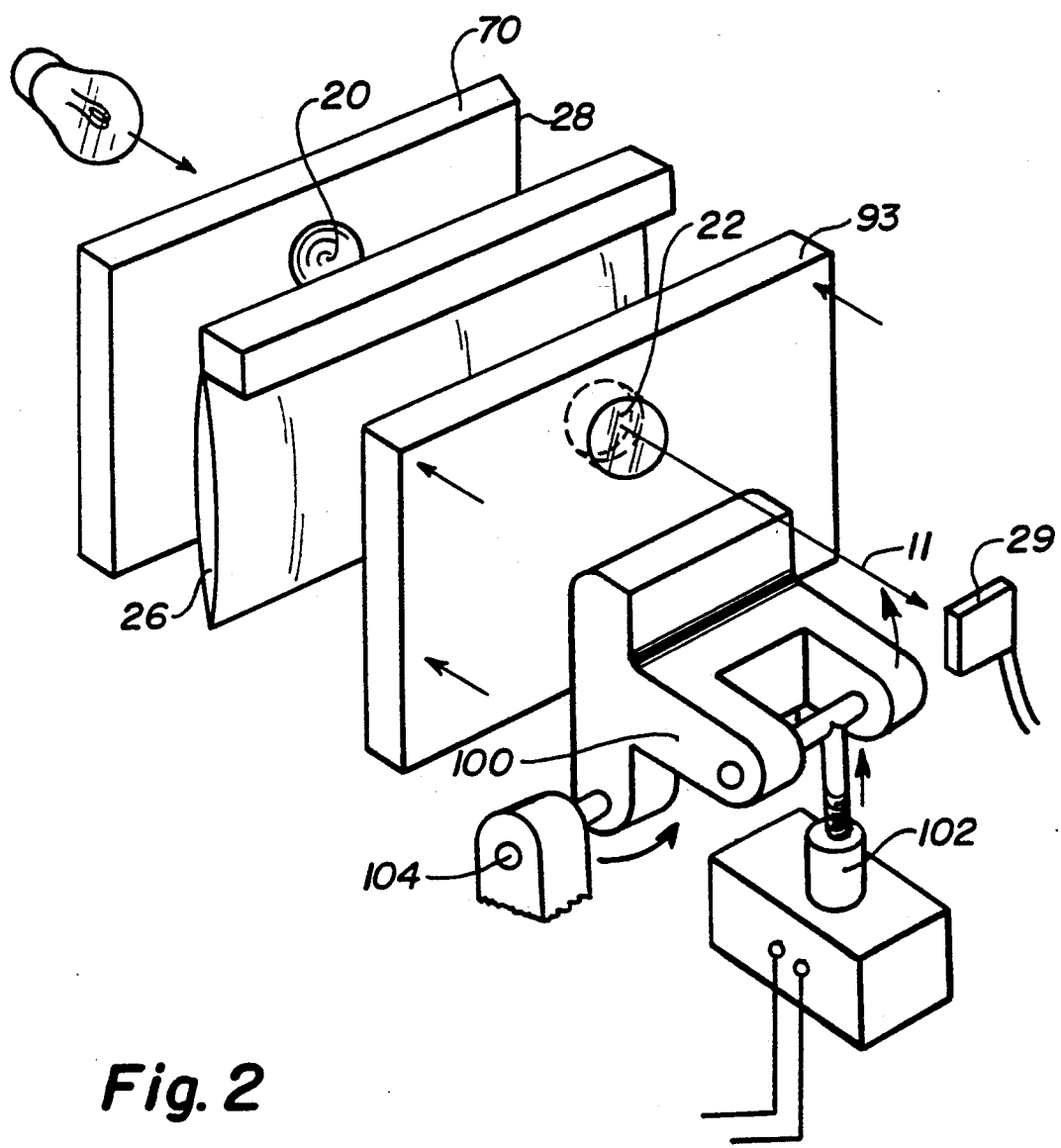
FIG. 2 is a pictorial representation of a mechanism suitable for holding the sample cuvette constructed in accordance with a preferred embodiment of this invention.

In a preferred embodiment of this invention, as best seen in FIG. 2, the first and second windows 20, 22 may be part of a cell or sample cuvette 26 forming device of the type described in U.S. Pat. Nos. 3,770,382 and 4,066 362 issued to Carter et al and used in the aca ® Automatic Clinical Analyzer. As is described by Carter et al. the windows 20, 22 define recesses in respective jaws 70, 93, the jaw 70 which forms the first window 20 being fixed, and the jaw 93 which may form the second window 22 being movable. If desired, the jaw 93 may be formed of an optical material, as previously described, with a recessed formed for the window 22. The sample cuvette in this case is an aca ® pack which has walls formed of flexible, transparent plastic film 38 (FIG. 1) as previously described. Thus when the jaws 70, 93 are brought together on the deformable part of a sample cuvette 26, the jaws 70, 93 squeeze the walls of the pack into the shape of the recess in the jaws thus forming the sample cell 26. The jaws may be actuated by any suitable mechanism. The mechanism used in the Automatic Clinical Analyzer sold by E. I. du Pont de Nemours and Company, Wilmington, Del. is suitable for this purpose. A simplified version of this mechanism is illustrated in FIG. 2 and includes a pivoted mechanical linkage 100 which is moved upwardly by a motor drive 102 to pivot about the pivot 104. This causes the jar of movable platen 93 to move toward the fixed platen 70 and form the aca ® pack 26 into an optical window as described.

As described in Carter et al., a fluid applicator is included to coat the surface between the pouch of the sample cuvette 26 and the windows 20, 22 with an optical coupling fluid. This fluid stabilizes any recesses between the pouch and the window formed by imperfections in the film from which the pouch is made and which would otherwise change dimensions during transmission measurements enough to introduce substantial error or form interference fringes.

The advantages of the apparatus of this invention are many. The use of a film pack that is separate from the windows 20, 22 simplifies the problem of coating bioactive material onto surfaces. It is generally easier to mechanize such coating onto film. Also, the cavity for the sample chamber 26 and prisms need not be cleaned after each use since they never become contaminated in the first place. The window geometry employed efficiently collects rays below a given angle of incidence. Precise alignment of the system is not necessary. Finally by allowing the light to enter the sample region below the critical angle, low F-number illumination optics can be employed. Further the exciting light is not attenuated before it strikes the area of interest.

EXAMPLE

Experiments were carried out by modifying the photometer of an aca ® IV Clinical Analyzer (E. I. du Pont de Nemours and Company, Wilmington, Del.). This photometer contains the means for pressurizing a sample pack between two windows, and for applying a refractive-index-matching oil between the film and the windows. The lamp was used with an excitation filter having a center wavelength of 530 nm, and a bandwidth of 10 nm (Corion Corp., Holliston, Mass., #P10-530-F). The standard lamp-side window platen was removed, and was modified to hold a quartz circular window with a face beveled 70°. from the plane of the window face. The beamsplitter holder was modified to hold detection optics at a 50° angle from the plane of the window face. Evanescent light was collected through a double-convex lens (Edmund Scientific Co., Barrington, N.J., #32860, 6 mm diameter, 6 mm focal length), an interference filter, (Corion Corp. #P70-650-A, 650 nm center wavelength, 70 nm bandwidth), and an aperture approximately 1 mm wide and 3 mm high. The lens was positioned to image the sample-window interface onto the aperture with a 2:1 demagnification.

The detector was a R1547 side-on ½"-diameter photomultiplier (Hamamatsu Corp., Bridgewater, N.J.) with a spectral response from 185 to 850 nm. The dynode resistors were each 200,000 ohms, and the anode was terminated in 50 ohms. Coaxial cable carried pulses to a photon counting system (Modern Instrumentation Technology, Inc., Boulder Colo., F-100T or equivalent). The photomultiplier was operated at 1000 volts, with a discriminator threshold that gave approximately 120 dark counts per second. Photon count rate was measured with a digital frequency meter (Hewlett-Packard Co., Palo Alto, Calif., 5300B, 5306, 5312A or equivalent). This was connected via HP-IB interface to a desktop computer (Hewlett-Packard Co. HP-85) which plotted the photon count rate as a function of time, and calculated the slope of the curve at one-minute intervals.

In order to demonstrate a sandwich immunoassay for Thyroid-Stimulating Hormone (TSH), a monoclonal antibody to TSH known as 972 was used. This antibody was developed by E. I. du Pont de Nemours and Company. Reagent chemicals were from Sigma Chemical Co., St. Louis, Mo. except as noted. The antibody was diluted to 1 mg/mL in a pH 7.0 phosphate buffer (5.42 g monosodium dihydrogen phosphate, 16.3 g disodium monohydrogen phosphate heptahydrate, 990 mL water). A 10% suspension of latex particles of 0.41 u diameter with a —COOH surface and a rhodamine dye were obtained from Bangs Laboratories, Inc., Indianapolis, Ind. One mL of antibody solution was mixed gently with 0.1 mL of 10% latex particle solution. To this was added 0.011 mL of a 10 mg/mL solution of EDAC, 1-ethyl-3(-3-dimethylaminopropyl) carbodiimide-HCl, in water. The particles, antibody, and EDAC were incubated overnight at room temperature, then centrifuged for 10 min at 10000 RPM. This resulted in coating of the particles with the antibody.

The next step was to overcoat the particles with bovine serum albumin (BSA), to reduce nonspecific binding. Ten mg/mL BSA was dissolved in phosphate buffer at pH 7.0. The particles were resuspended by vigorous vortex mixing and sonication in 1 mL of this solution, incubated for 2 hr at room temperature on a rocker table, and centrifuged as above.

It is necessary to wash the particles thoroughly, since any antibody shed during the assay will inhibit signal generation. This was accomplished by resuspending the particles in 1 mL of 15 mg/mL glycine and 0.1 mg/mL sodium dodecyl sulfate in phosphate buffer, pH 7.0, and then washing (by centrifugation as above) the particles three times in this buffer.

The particles were stored at 4° C. in a solution of 15 mg/mL glycine.

To form the other half of the sandwich assay, aca ® packs were coated with a second monoclonal antibody to TSH, known as 4/46. This antibody was diluted to 0.1 mg/mL in citrate-phosphate buffer, pH 4.8, 0.15 M NaCl, 0.1 mg/mL sodium azide (antibody coating buffer). Unsealed, unfilled aca ® sample packs were obtained. A rubber dam was placed over the inside of the pack, with a 15 mm diameter hole over the area of the pack which is illuminated in the photometer. Into that hole was placed 0.75 mL of the antibody solution. This was incubated for 1 hr at room temperature, aspirated, and then washed three times with the antibody coating buffer described above.

The film was then treated to minimize nonspecific binding with 0.75 mL of blocking solution, 50 mg/mL BSA, 1 mg/mL Tween ®-20, 0.05 M NaCl in phosphate buffer, pH 7.0. This was incubated for 1 hr at room temperature, and aspirated. A second coating was done in a similar blocking solution, except the Tween ®-20 was replaced with 50 mg/mL trehalose, and the NaCl was omitted. This solution was aspirated, and the packs were allowed to dry for 3 hr in a dry room at 22° C. The packs were then sealed on a heat-sealing machine used in pack manufacture.

An assay buffer of Sigma phosphate-buffered saline (12 mM phosphate, 120 mM NaCl, pH 7.5) with 1 M added NaCl and 0.05% Tween ®-20 was used. Calibrators consisted of horse serum containing added amounts of purified TSH. Two mL of assay buffer and 0.5 mL of each calibrator were pre-mixed and then added to an aca pack prepared as above. The packs were incubated for 15 min at room temperature. This was followed by the addition of 0.5 mL of the antibody-coated latex prepared above in 2 mL of assay buffer. The packs were then placed into the photometer, and the jaws were closed to pressurize the cuvette. Reaction rates were measured from 120 sec to 420 sec after the jaws were closed. Results were as follows:

| TSH Concentration | Photon Counts/sec/min Rate Signal |
|---|---|
| 50 uIU/mL | 1097 CPS/min |

-continued

| TSH Concentration | Photon Counts/sec/min Rate Signal |
| --- | --- |
| 0.5 uIU/mL | 530 CPS/min |
| 0 uIU/mL | 420 CPS/min |

These results demonstrate a relationship between the dose of TSH present and the rate of particle binding to the cuvette wall.

We claim:

1. Apparatus for optically detecting an analyte of interest by separating bulk and evanescent emission from a tag capable of producing inelastic scattering of excitation radiation, comprising:

an optically transparent sample holder having an inner wall and holding a sample having the tag, means for binding the tag to the inner wall immobilized on the inner wall, wherein at least a portion of the tag is bound to the inner wall in the presence of the analyte, a prism connecting the sample holder contiguous the inner wall to provide an optical interface with the sample, the prism having an exit surface, and means to excite the sample and tag to produce bulk emission and evanescent emission such that the bulk emission reaches the exit surface at an angle of incidence with the exit surface which is greater than the critical angle, whereby the bulk emission is totally internally reflected and the evanescent emission is passed through the exit surface.

* * * * *